(12) United States Patent
Pennings et al.

(10) Patent No.: US 9,161,874 B2
(45) Date of Patent: Oct. 20, 2015

(54) MEDICAL WASTE DISPOSAL APPARATUS

(75) Inventors: Bert Pennings, Dandenong South (AU); Chris Hart, Berwick (AU)

(73) Assignee: Catilina Nominees Pty Ltd, Dandenong South, Victoria (AU)

( * ) Notice: Subject to any disclaimer, the term of this patent is extended or adjusted under 35 U.S.C. 154(b) by 0 days.

(21) Appl. No.: 13/634,803

(22) PCT Filed: Mar. 30, 2011

(86) PCT No.: PCT/AU2011/000356
§ 371 (c)(1),
(2), (4) Date: Jan. 17, 2013

(87) PCT Pub. No.: WO2011/120083
PCT Pub. Date: Oct. 6, 2011

(65) Prior Publication Data
US 2013/0113171 A1    May 9, 2013

(30) Foreign Application Priority Data

Mar. 30, 2010 (AU) .................................. 2010901336

(51) Int. Cl.
*A61G 12/00* (2006.01)
*B62B 3/04* (2006.01)
*A61B 19/02* (2006.01)
*B62B 3/00* (2006.01)
*B65F 1/14* (2006.01)
*A61B 19/00* (2006.01)
*A61B 17/06* (2006.01)
(Continued)

(52) U.S. Cl.
CPC .............. *A61G 12/001* (2013.01); *A61B 19/00* (2013.01); *A61B 19/0248* (2013.01); *A61B 19/0287* (2013.01); *B62B 3/004* (2013.01); *B65F 1/141* (2013.01); *B65F 1/1468* (2013.01); *B65F 1/163* (2013.01); *B65F 1/1615* (2013.01); *A61B 17/06133* (2013.01); *A61B 19/0288* (2013.01); *A61B 2017/00973* (2013.01); *A61B 2019/025* (2013.01); *A61B 2019/0209* (2013.01); *A61B 2019/0221* (2013.01); *B62B 2202/20* (2013.01); *B65F 2001/1676* (2013.01); *B65F 2210/18* (2013.01)

(58) Field of Classification Search
USPC .............. 280/47.34, 47.35, 79.11, 79.2, 79.3, 280/33.998; 220/23.87, 262, 263, 264
See application file for complete search history.

(56) References Cited

U.S. PATENT DOCUMENTS 4,165,088 A * 8/1979 Nelson ........................ 280/47.35
4,576,307 A * 3/1986 Frydenberg .................... 220/324
4,615,464 A * 10/1986 Byrns .......................... 220/4.23
(Continued)

FOREIGN PATENT DOCUMENTS

DE   199 12 563 A1   9/2000
GB    2 257 022 A    1/1993
WO  WO 2008/100586 A1  8/2008

OTHER PUBLICATIONS

International Search Report for corresponding International Patent Application No. PCT/AU2011/000356 mailed May 30, 2011.

*Primary Examiner* — Frank Vanaman
(74) *Attorney, Agent, or Firm* — Merchant & Gould P.C.

(57) ABSTRACT

A trolley (10) for a medical waste container (12) is provided for use in a medical treatment facility such as an operating theatre or other hospital or medical environment. A cart (100) is provided for transporting a collection of medical waste containers (12) throughout a medical treatment facility.

19 Claims, 9 Drawing Sheets

(51) Int. Cl.
*A61B 17/00* (2006.01)
*B65F 1/16* (2006.01)

(56) References Cited

U.S. PATENT DOCUMENTS

| | | | | |
|---|---|---|---|---|
| 4,821,903 | A * | 4/1989 | Hayes | 280/47.26 |
| 4,875,696 | A * | 10/1989 | Welch et al. | 280/47.34 |
| 6,352,225 | B1 | 3/2002 | Dooley et al. | |
| 6,460,950 | B2 * | 10/2002 | Spitzer et al. | 312/249.8 |
| 6,659,476 | B2 * | 12/2003 | Weida | 280/47.19 |
| 7,014,197 | B2 * | 3/2006 | Baldwin et al. | 280/47.27 |
| 7,464,945 | B2 * | 12/2008 | Humphries et al. | 280/47.26 |
| 7,866,679 | B1 * | 1/2011 | Leon | 280/79.5 |
| 2007/0068942 | A1 | 3/2007 | Smudde | |
| 2009/0145901 | A1 | 6/2009 | Finnestad et al. | |

* cited by examiner

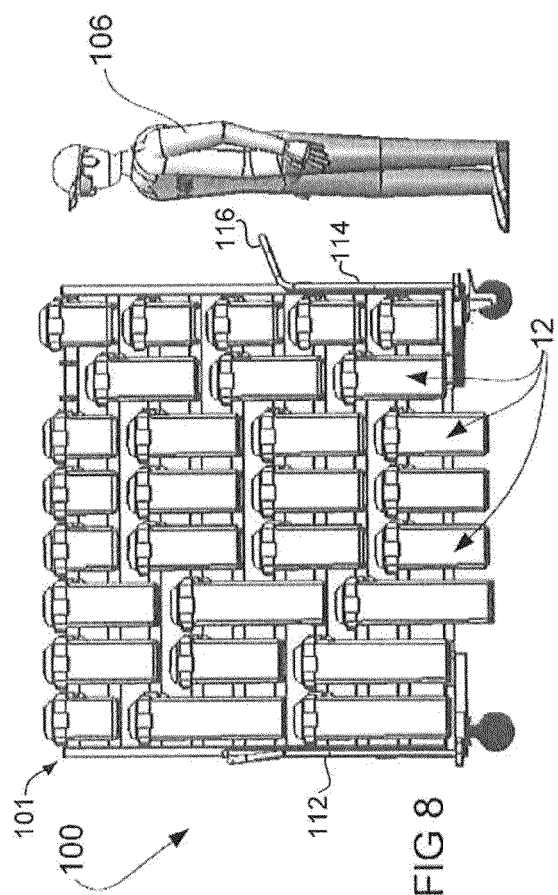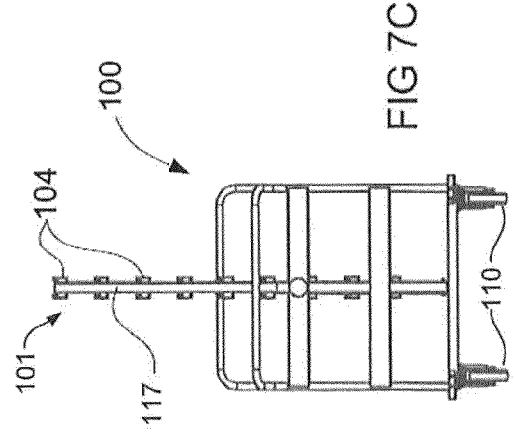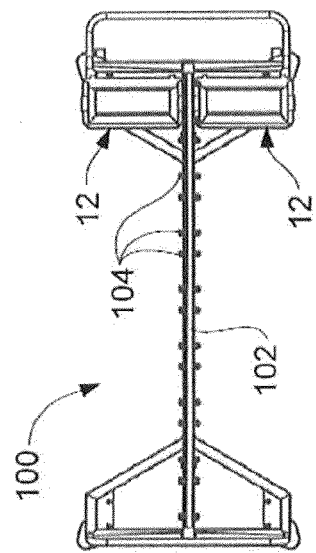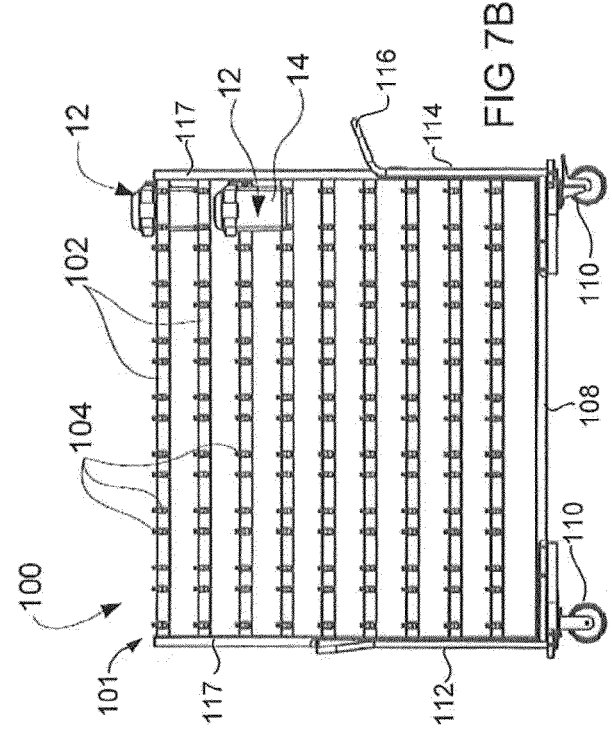

MEDICAL WASTE DISPOSAL APPARATUS

This application is a National Stage Application of PCT/AU2011/000356, filed 30 Mar. 2011, which claims benefit of Ser. No. 2010901336, filed 30 Mar. 2010 in Australia and which applications are incorporated herein by reference. To the extent appropriate, a claim of priority is made to each of the above disclosed applications.

TECHNICAL FIELD

The present invention relates to a trolley for a medical waste container for use in a medical treatment facility such as an operating theatre or other hospital or medical environment. The invention also relates to a cart for transporting a collection of the medical waste containers throughout the medical treatment facility.

BACKGROUND

Medical treatment facilities generate a lot of disposable medical waste, for example sponges, gauze, drapes, bandages etc. and sharps of various types. Such waste is usually contaminated with the blood or body fluids of a patient, which biohazards can possibly expose medical staff or other patients to infectious diseases should they accidentally come into contact with the medical waste. Thus such medical waste requires special handling immediately following its generation and continuing through to its ultimate destruction.

Waste medical sharps may be disposed of separately to non-sharps medical waste into specially constructed containers, which allow ready disposal of a used sharps whilst also preventing hand access into the container. Other types of containers for medical waste more generally (that is for receiving all types of medical waste), are relatively large with large area openings for receiving bulky items (for example drapes or sheets). These types of containers are more suitable for quick disposal of medical waste virtually immediately upon its generation as waste. Thus in addition to being of relatively large size and with a large area opening, such containers ideally are floor positionable and readily maneuverable so as to be placeable conveniently near the medical waste generation site, which may for example be a hospital operating theatre. Also, ideally, the medical waste disposal system should be such as to minimally require hand contact with the containers thereof at least up until the containers, after having been filled with medical waste (filled is defined herein below), are sealed and locked. Handling of the containers prior to them being sealed and locked could potentially expose an individual to the contaminated waste.

The present invention seeks to provide medical waste containment apparatus that is improved compared to prior art apparatus at least in respect of minimising hand contact for setting up and filling a container for the medical waste.

The term "filled", including "fill" and "filling", throughout this specification is to be understood as meaning that a container contains some medical waste without the container necessarily being full or filled up with the medical waste.

The above Background discussion is included to explain the context of the present invention. It is not to be taken as an admission that any of the documents or other material referred to was, in Australia, published, known or part of the common general knowledge at the priority date established by this application.

DISCLOSURE OF THE INVENTION

According to the present invention there is provided a trolley for a container for medical waste, the container having a receptacle for receiving medical waste and a lid for sealing the receptacle, the lid being pivotable between an open position and a closed position, the lid and receptacle being shaped so that an undersurface portion of the lid is accessible when the lid is in the closed position, the trolley including a retainer for retaining the container on the trolley, and a member having a lid engaging portion, the member being operable so that the lid engaging portion engages the undersurface portion of the lid and pivots the lid from the closed position to the open position, wherein the retainer and member are relatively located such that when the container is installed on the trolley and retained by the retainer, the lid engaging portion becomes positioned adjacent the undersurface portion of the lid without requiring manual manipulation of the member or lid.

The container is thus easily installed onto the trolley ready for use. The relative location of the retainer and member mean that when the container is installed on the trolley by an operator, no hooking or other manipulation of the member or lid by an individual for the member and lid to engage or be in contact for the member to be able to open the lid is required. This saves the operator time and makes incorrect installation unlikely. Also, as the lid engaging portion engages an undersurface portion of the lid that is accessible when the lid is in the closed position, the member does not interfere with a seal between the lid and receptacle of the container.

The member may be a lever, providing a simple means of operation. The lever, for example, may pivot in a plane with the lid engaging portion extending transverse to the plane. Alternatively, the member may be a rod that pushes the undersurface portion from below. A further alternative may have the lever including a pair of arms locatable on opposing sides of the lid to lift underside portions located on both sides of the lid.

The retainer may be shaped to allow the container to be installed downwards on the trolley, for example it may be a bracket. Further, the lid engaging portion may be positioned to engage an undersurface portion on a side of the lid. These features in combination allow easy installation of the container as the lid engaging portion does not interfere with the container during downwards installation. As an additional feature, the bracket may have a tongue to prevent over-pivoting of the lid.

The member may be operable by a foot pedal for ease of opening the container. The pedal may be biased so that the member allows the lid to return to the closed position (for example due to the weight of the lid). Where the member is a lever, a cable may extend between the foot pedal and the lever to allow operation of the member. Alternatively a linkage may be provided between the pedal and the lever. The linkage may be in the form of push rods and a further lever. These preferred embodiments provides a simple robust operation.

According to another aspect, the present invention provides apparatus for medical waste including: a container having a receptacle for receiving medical waste and a lid for sealing the receptacle, the lid being pivotable between an open position and a closed position, the lid and receptacle being shaped so that an undersurface portion of the lid is accessible when the lid is in the closed position, wherein the container is installed on a trolley as described above.

Conveniently, the receptacle of the container may have a top lip that has a cut away section, and the undersurface portion of the lid may be part of the lid that projects over the cut away section. The lid of the container may be biased closed, for example due to the weight of the lid.

The invention also provides a cart for collecting several filled, locked and sealed recyclable medical waste containers for transfer to a central despatch location within the medical treatment facility and for re-distributing returned sterilised empty recyclable medical waste containers to locations within the medical treatment facility, the cart including a rack having a plurality of generally horizontal rails wherein each rail includes retainers for retaining several of the medical waste containers on the rack, wherein the retainers are such that the several medical waste containers are maintained separated from each other.

The medical waste containers are maintained separated from each other to prevent them rubbing together as they are being transported by the cart which could damage their appearance. Commercially it is desirable that the recyclable containers remain or be kept in as pristine condition as possible. If such containers receive cosmetic damage, they are typically buffed or polished to restore their pristine appearance. Keeping the recyclable medical waste containers separated whilst transporting them largely avoids the need for them to be buffed or polished and thus saves costs.

Preferably the retainers are hooks. They could alternatively be slide-on bars which are receivable within complementary fittings on the recyclable medical waste containers.

The rack of the cart may be removably attached to the cart such that it can be independently utilised to store the recyclable medical waste containers at a convenient location within the medical treatment facility ready for distribution.

For a better understanding of the invention and to show how it may be performed, embodiments thereof will now be described, by way of non-limiting example only, with reference to the accompanying drawings. It is to be understood that the particularity of the drawings does not supersede the generality of the definition of the invention provided by the claims.

BRIEF DESCRIPTION OF THE DRAWINGS

FIGS. 7A to C are, respectively, a plan, a side elevation and an end elevation of a cart for transporting recyclable medical waste containers, and FIG. 8 illustrates the cart of FIG. 7 with recyclable waste containers loaded thereon.

DETAILED DESCRIPTION

Figure 1:
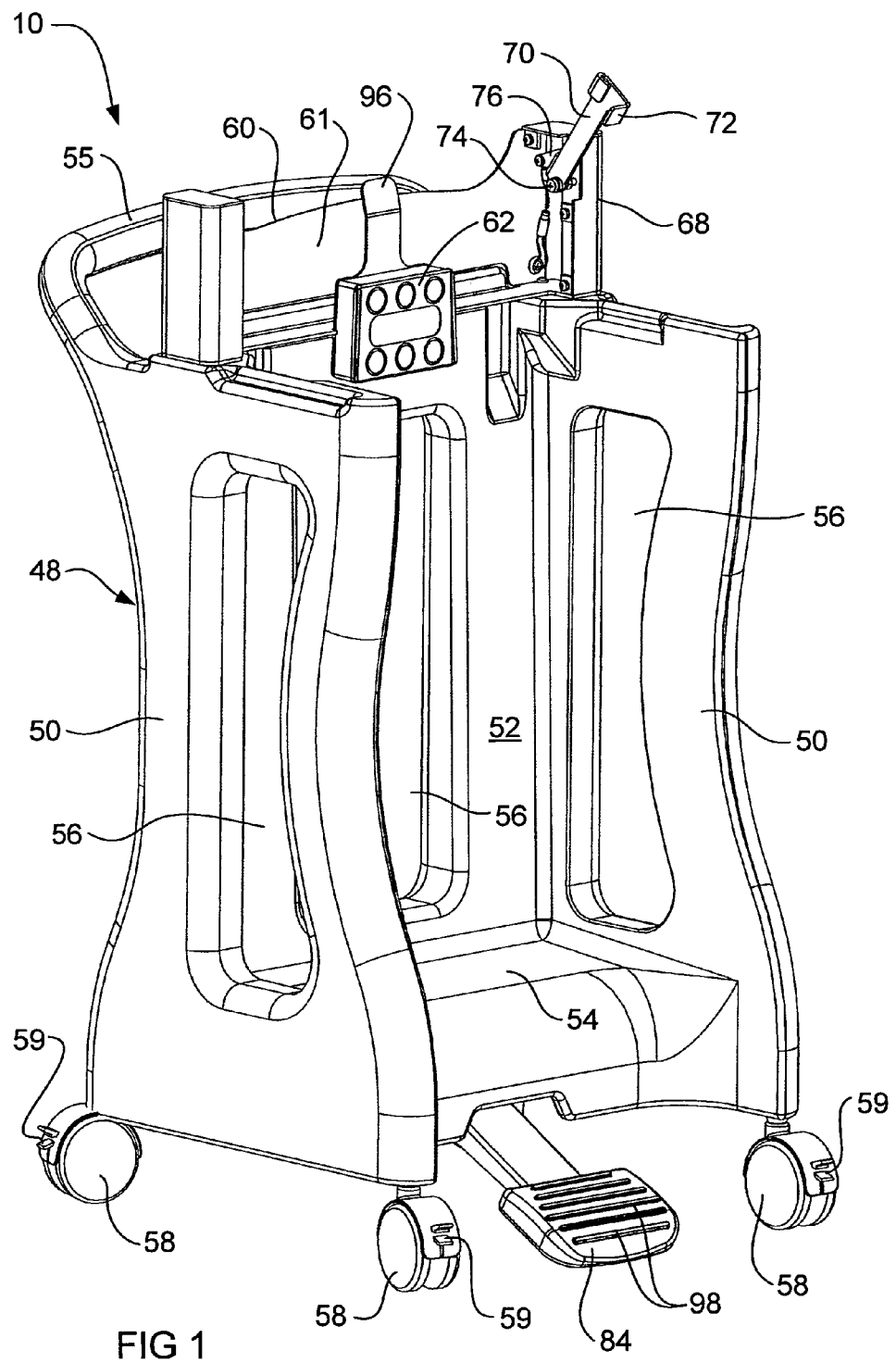
FIG. 1 is an isometric view of a trolley for a recyclable container for medical waste in accordance with one embodiment of the invention.
Figure 2:
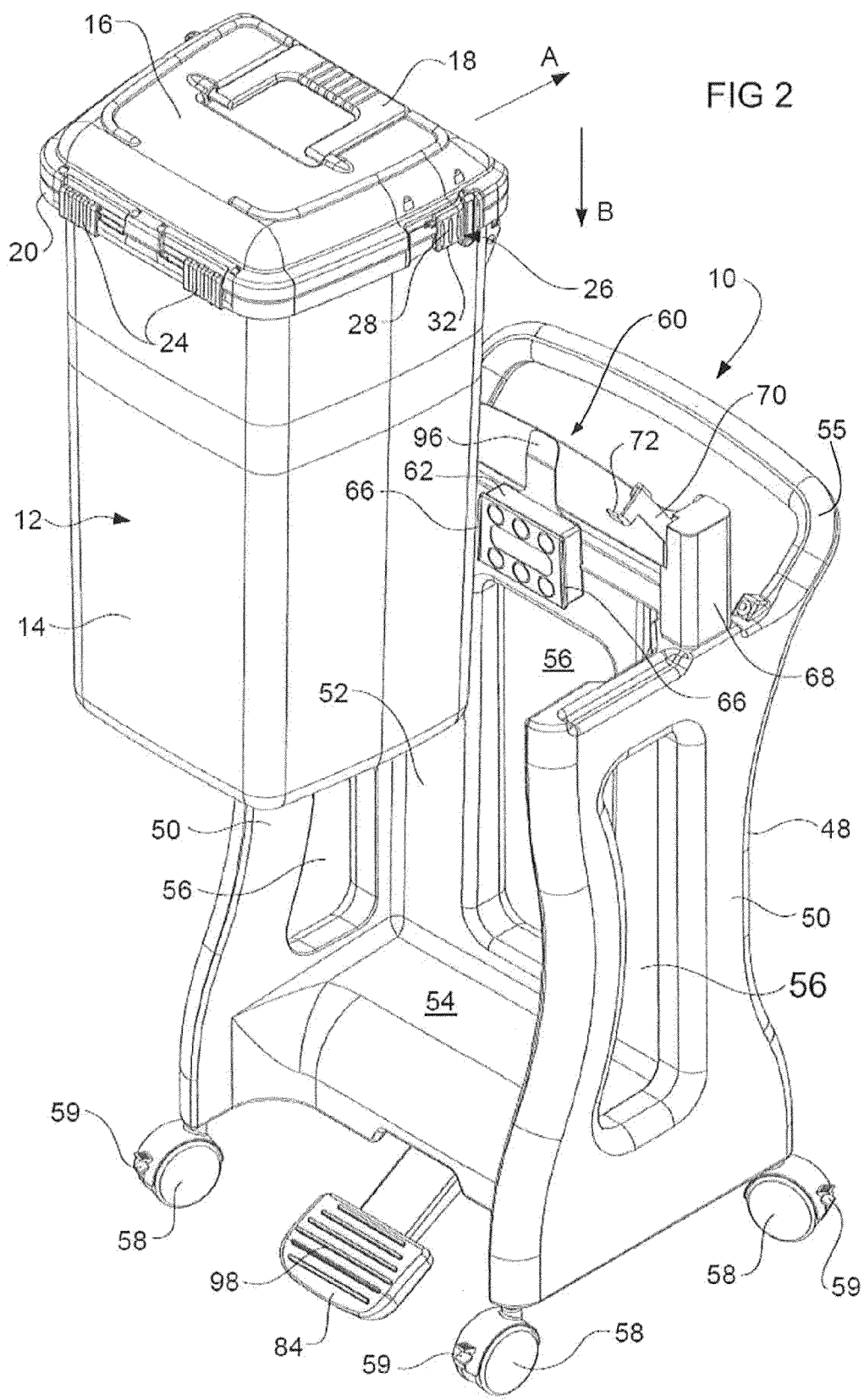
FIG. 2 is an isometric view of the trolley of FIG. 1 with a recyclable container ready to be installed on the trolley with the lid of the container in a closed position.

With reference to FIGS. 1-4, a trolley 10 may be used to hold a recyclable container 12 for medical waste that is generated in a hospital or other medical facility, such as an operating theatre. The container 12 comprises a receptacle 14 with a pivotable lid 16 having a handle 18. The receptacle 14 includes a top rim 20 having a flat upper surface against which a seal 22 (see FIG. 4) in the periphery of the lid 16 seals when the lid 16 is held in its closed position on the receptacle rim 20. The lid 16 may be held closed on the rim 20 by two slidable latches 24 carried by the receptacle's rim 20. The latches 24 can be unlatched to allow the lid 16 to be pivoted to an open position. At each side of the container 12 and carried by the lid 16 is a lock 26 for locking the lid 16 to the receptacle 14. Thus when the receptacle 14 is filled (as hereinbefore defined) with medical waste, the lid 16 is latched closed by the latches 24 and then locked closed by the locks 26. Once locked, the locks 26 can only be unlocked at a medical waste disposal centre.

Each lock 26 includes a slidable member 28 mounted on the lid 16, having a depending portion that, in the unlocked position is positioned within a cutaway section 30 (see FIG. 4) of the rim 20 of the receptacle 14. A bottom surface 32 of the right hand (looking at the front of the container 12) slidable member 28 provides an under surface portion of the lid 16 that is accessible when the lid 16 is closed for engagement by a member (to be described below) for opening the lid 16.

Figure 3:
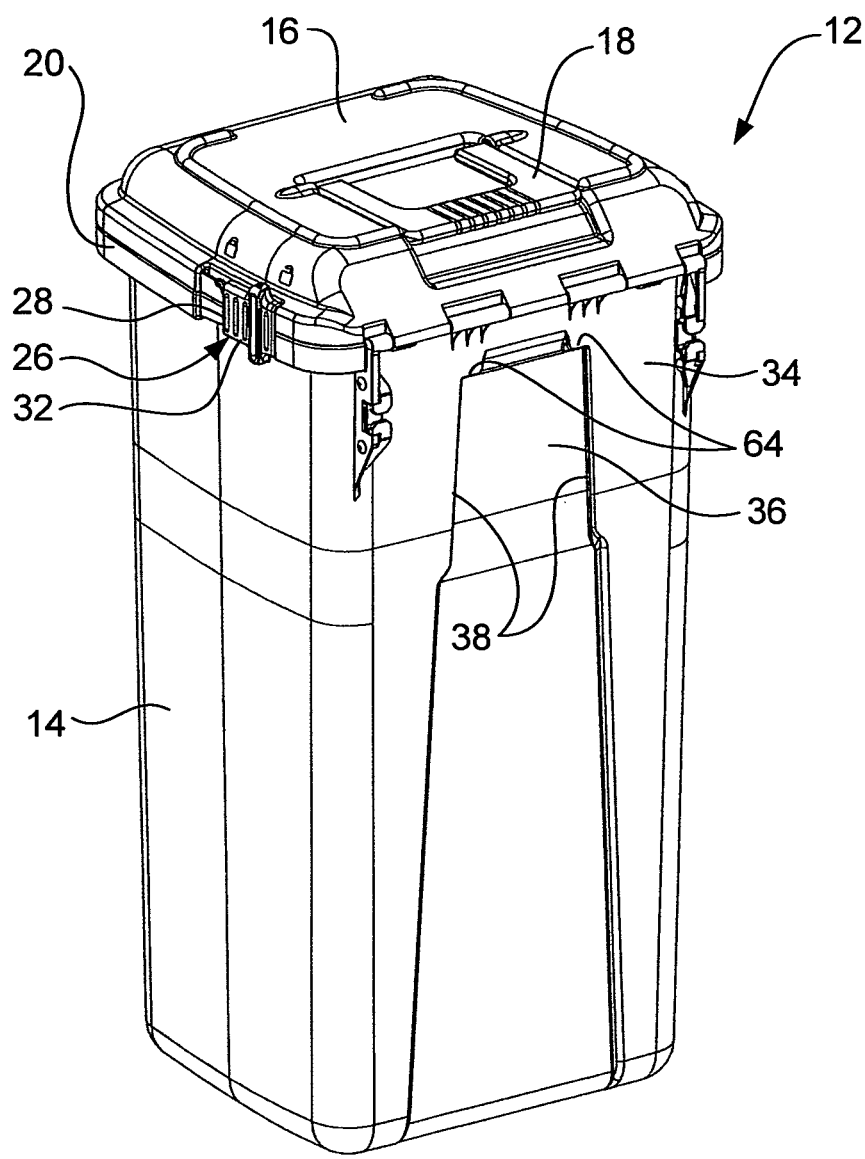
FIG. 3 is an isometric rear view of the recyclable container of FIG. 2.
Figure 4:
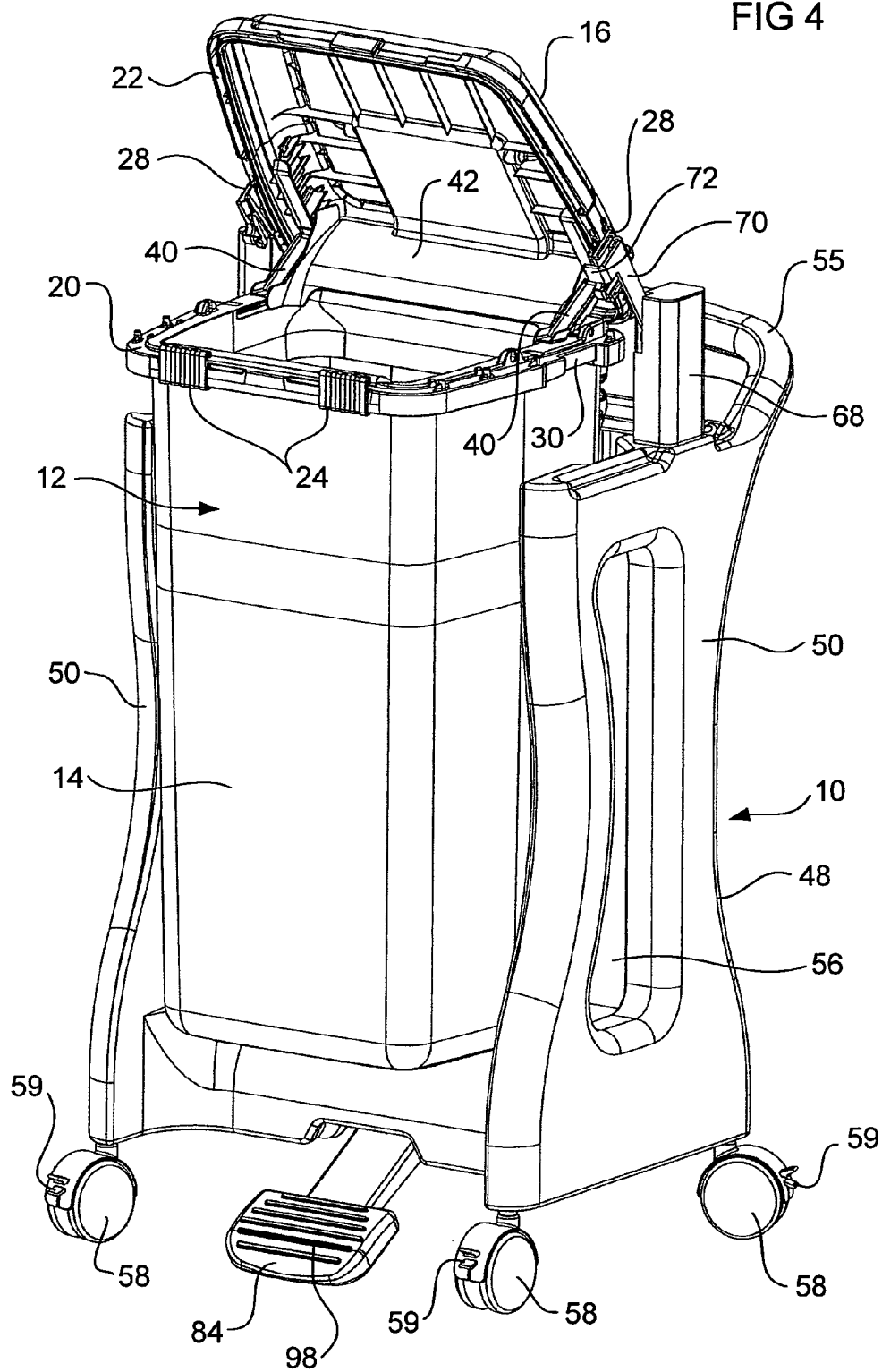
FIG. 4 is an isometric view of the trolley of FIG. 1 with a recyclable container installed thereon with its lid in an open position.

The receptacle 14 of the container 12 also includes, in a rear surface 34, a dovetail shaped (in cross-section) recess 36, that is, a recess with undercut edges 38 (see FIG. 3). The edges 38 also converge towards one another towards the lid 16. This is for mounting the container 12 on a retainer (to be described below) of the trolley 10.

The receptacle 14 of container 12 and its lid 16 are moulded from a tough plastic, for example Acrylonitrile Butadiene Styrene (ABS), and include parts that are not germane to the present invention, for example pivot guides 40 for the lid 16 and shields 42 to ensure safe deposit of medical waste into the receptacle 14. These and other features of the container 12 are not further described as they do not affect the present invention. However it is to be noted that the container 12 is relatively large (noting that different sized receptacles 14, for example depth wise, may be used) and that when the lid 16 is open, a relatively large area access opening into the receptacle is available (see for example FIG. 4).

Considering now the trolley 10, this comprises a moulded plastic frame 48 (for example rotationally moulded from polyethylene) having sides 50, a rear wall 52 and a base 54 providing a space for receiving a container 12. The frame 48 also includes a handle 55. The sides 50 and rear wall 52 are formed with cut out sections 56 to save material and reduce the weight of the trolley 10. The sides 50 towards their bottom, extend forwards and each has a relatively large castor wheel 58 attached at the bottom. Two other castor wheels 58 are attached at the rear. The four castor wheels 58 are spaced to ensure stability of the trolley 10, particularly when a full container 12 is mounted thereon, that is, the castor wheels 58 are spaced such that the trolley 10 is not easily tippable. The size of the castor wheels 58 are also such that the trolley 10 is easily wheelable from location to location, and is readily maneuverable at a location to be optimally positioned for medical waste to be disposed into a container 12. The castor wheels 58 are lockable by levers 59 such that once positioned and the wheels 58 locked, the trolley 10 is stably maintained in position. To assist maneuverability of the trolley 10, the handle 55 extends across the width of the frame 48, is at a comfortable height for an average person, and is of a diameter that is comfortable for gripping.

On the top of the frame 48 is fixed an assembly 60 (see FIG. 6) on the centre of a metal part 61 of which is fixed a retainer 62 which in this embodiment is a bracket. The retainer 62 has a size and shape that is complementary to the recess 36 in the rear surface 34 of the container 12, such that the container 12 is mountable on the trolley 10 by, from a relatively raised position of the container 12, moving it backwards (see arrow A of FIG. 2) until the recess 36 is positioned above the retainer 62, and then moving the container 12 downwardly (see arrow B of FIG. 2) for the retainer 62 to enter the recess 36. The retainer 62 bears against top corner edges 64 of the recess 36 and lateral ribs 66 of the retainer 62 (see FIG. 6) are located within the undercut edges 38. Thus the container 12 is retained on the trolley 10 by the retainer 62.

In a side post 68 (that is, the right hand side post as viewed in FIG. 6) of the assembly 60 is located a member 70 in the form of a pivoted lever, having a lid engaging portion 72. When a container 12 is installed on a trolley 10 (as described above with reference to FIG. 2), the lid engaging portion 72 engages the undersurface portion of the lid 16 (that is, the bottom surface 32 of the right hand slidable member 28 as described above). Thus the retainer 62 and member 70 (which in this embodiment is a lever) are relatively located such that when the container 12 is installed on the trolley 10 and retained by the retainer 62, the lid engaging portion 72 is positioned adjacent the undersurface portion 32 of the lid 16, ready for the member 70 to be operated to pivot the lid 16 from the closed position to an open position, without requiring any manual manipulation of the member 70 or the lid 16.

Figure 6:
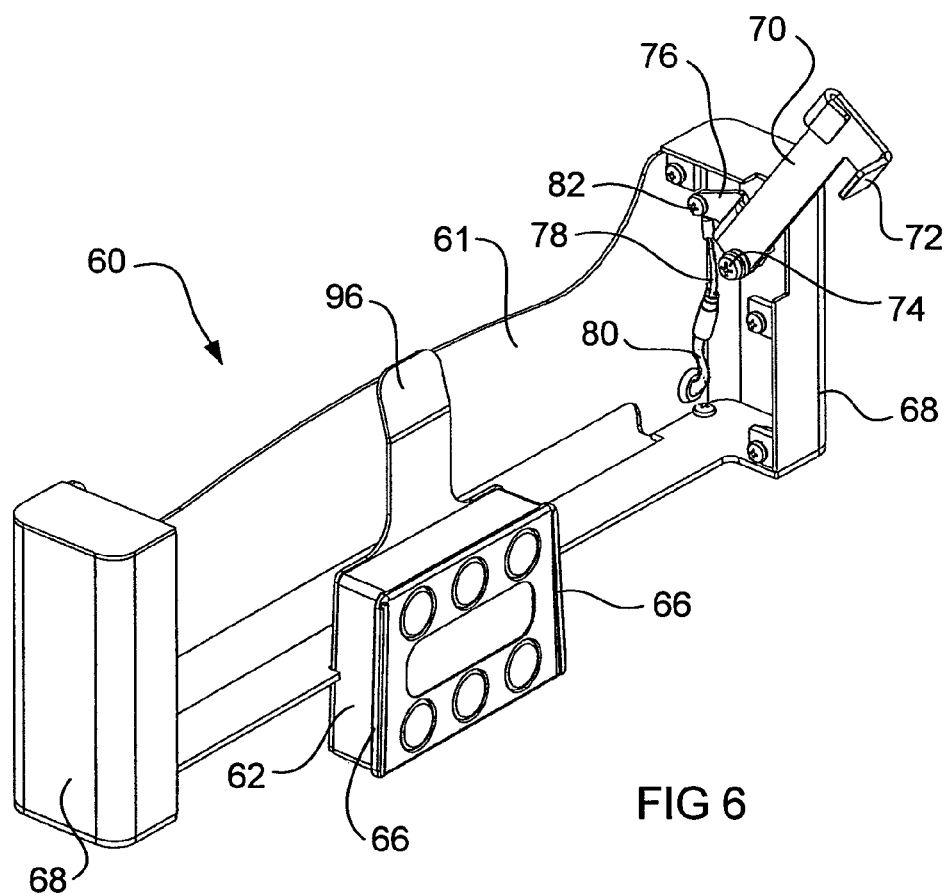
FIG. 6 is an isometric view of a component of the trolley of FIG. 1 illustrating a member for opening the lid of a recyclable container and a retainer for retaining the container.

In FIG. 6 a cover plate of the post 68 has been removed to allow illustration of details of the member 70. The member 70 in the form of a lever is pivotally mounted by a bolt 74 to the metal part 61 of the assembly 60. The lever member 70 includes a lateral extension 76 to which the internal wire 78 of a Bowden cable 80 is fixed at 82. When the wire 78 of the cable 80 is drawn into the sheath of cable 80, which is by depression of a foot pedal 84 of the trolley 10, the lever member 70 is pivoted about bolt 74 such that its lid engaging portion 72 engages the undersurface portion 32 of the lid 16 to pivot the lid from its closed position to an open position. The Bowden cable 80 passes through a rear surface of the metal part 61 and directly travels to the foot pedal 84 through the frame 48.

Figure 5:
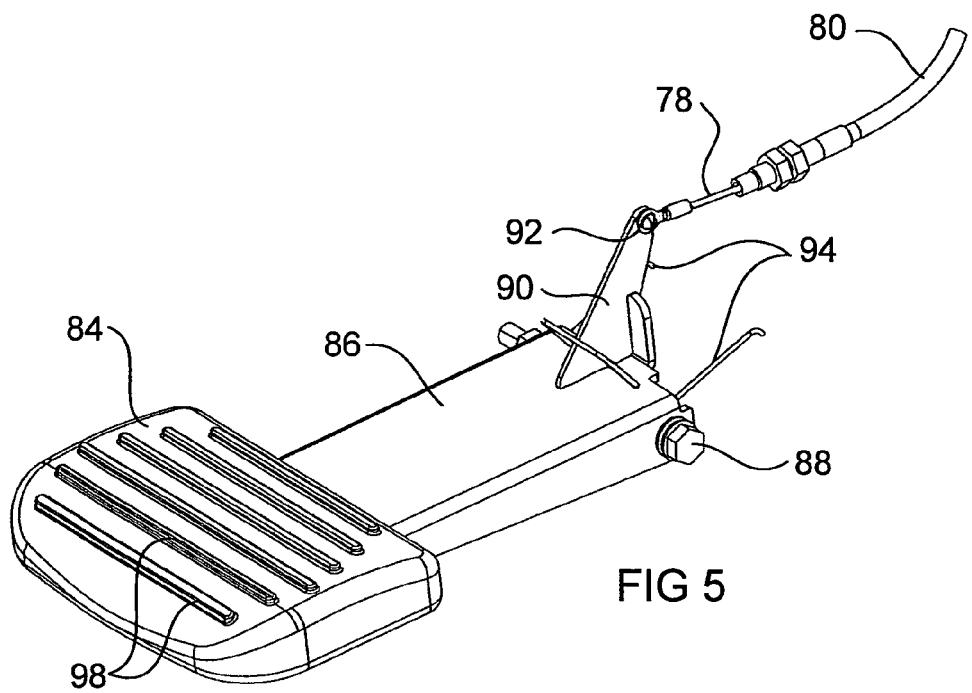
FIG. 5 is an isometric view of the foot pedal of the trolley of FIG. 1.

With reference to FIG. 5, the foot pedal 84, for example of polyethylene, is on a lever arm 86 which is pivotally mounted (not shown but via a bolt 88) to a bracket (not shown) that is fixed to the undersurface of the base 54 of the frame 48. The lever arm 86 includes an upstanding projection 90 to which an end 92 of the internal wire 78 of the Bowden cable 80 is fixed (note that in FIG. 5 the end 92 is not shown as fixed to the projection 90, but it would be obvious to a skilled person how to so fix it). The sheath of the Bowden cable 80 is fixed to the frame 48. Thus when the foot pedal 84 is depressed, the projection 90 withdraws the internal wire 78 from the sheath of cable 80 which correspondingly draws the other end of the internal wire 78 into the sheath at the lever member 70, thus pivoting the lever member 70 upwardly. This position is illustrated by FIG. 1.

The bolt 88 of the foot pedal lever arm 86 has a spring (not shown) associated with it which has portions 94 which bear against the undersurface of the base 54 and another portion (not shown) which bears against a undersurface of the foot pedal lever arm 86 to bias it upwardly relative to the frame 48. Thus when a depressing force is removed from the foot pedal 84, the spring biases the foot pedal upwardly to return to its non-operated position. This allows the cable 80 to return the lever member 70 to its non-operated position, which allows the lid 16 by gravity to return to its closed position.

The retainer 62 includes an upstanding tongue 96 to prevent over-pivoting of the lid 16 when it is opened, for example, the tongue 96 may limit the lid 16 to pivot to a 60 degree angle.

The foot pedal 84 is relatively large and the sides 50 and base 54 of the frame 48 are arranged such that there is a wide angle of access to the foot pedal 84. The foot pedal 84 is also formed with prominent ribs 98 to reduce the possibility of an operator's foot slipping off. Thus the foot pedal 84 is readily accessible to an operator and is easily depressed to open the lid 16 of a container 12. Also, the Bowden cable 80 is such that when an operator removes his/her foot from the pedal 84 and it returns to its non-operated position due to the spring bias, the lid 16 does not "slam" closed, but instead steadily closes. This reduces the possibility of possibly contaminating aerosols within the receptacle 14 from being "blown out" as may occur if the lid 16 slams closed.

The foot pedal 84 operating a lever 72 with the lid engaging portion 72 via the Bowden cable 80 provides a relatively simple yet very effective and efficient mechanism for pivotally opening the lid 16 of a recyclable container 12. This stands in contrast to prior art apparatus which involve more complex mechanisms to, for example, slide open a reciprocatable lid, or require a person to physically touch a container and an operating part of a trolley to couple them together. The present invention provides structures which reduce the need for hand contact when manipulating unsealed, unlocked containers (which may possibly contain some medical waste).

Disposal of medical waste is very expensive and in order to alleviate some of the cost, the present invention involves the use of recyclable medical waste containers 12. To further reduce costs efficiencies can be realised in collecting filled containers for the medical waste to be destroyed and then distributing empty sterilised containers within a medical treatment facility.

For example a system for disposing of medical waste using the recyclable waste containers 12, wherein respective ones of the recyclable waste containers 12 are variously locatable within a medical treatment facility and each recyclable waste container 12, after being filled (as hereinbefore defined) with medical waste, is sealable and lockable, involves the use of a cart 100. Such a cart is illustrated in FIGS. 7A to C and 8. It is for collecting several of the filled, locked and sealed recyclable waste containers 12 for transport to a central despatch location within the medical treatment facility and for redistributing returned sterilized empty recyclable waste containers 12 to locations within the medical treatment facility.

Referring to FIGS. 7A to C and 8, the cart 100 includes a rack 101 with a plurality of generally horizontal rails 102 on which are located hooks 104 which are located and spaced such that the top rim 20 of a container 12 can be hooked over two of the hooks 104. These two hooks are spaced such that a container 12, when so hooked onto the rack 101 of the cart 100, cannot move forwardly or backwardly along a rail 102 to any appreciable amount. Also the depth of the receptacles 14 of containers 12 mounted onto the rails 102 is such that the hooks 104 on a lower rail 102 contact the receptacle 14 near its base and thus hold it away from the lower rails 102. Thus each container 12 is maintained separated from each other container 12. A cart 100 having a rack 101 with rails 102 and hooks 104 that are appropriately spaced for the containers 12, allows the filled, sealed and locked containers 12 to be easily and quickly loaded onto and off the cart 100 thus saving handling time. Separation between the containers 12 is maintained so they do not rub against each other thus damaging their appearance. Being recyclable, if their appearance is damaged, the containers 12 after being emptied and sterilized, would need to be buffed or polished to restore their cosmetic appearance to maintain their commercial viability. Avoiding any need for such buffing and polishing further saves costs.

The cart 100 may comprise a base 108 having four spaced relatively large castor wheels 110. The base 108 includes upright front and rear end frames, respectively 112, 114 and has a handle 116 that extends from the upper end of the rear frame 114.

The rack 101, which comprises opposite vertical side beams 117 between which the rails 102 extend, may be removably attached (not shown) to the base 108 and end frames 112, 114. This allows for the rack 101 to be used independently of the cart 100 to store recyclable medical waste containers 12 at a convenient location within the medical treatment facility ready for distribution. The rack 101, for example, could be wall mounted at the convenient location.

The cart 100 is sized such that it is easily maneuverable by an operator 106 taking into account applicable occupational health and safety regulations. It is also sized so as to easily fit within corridors and/or lifts of a medical treatment facility. The cart 100 is used to collect and transport filled, sealed and locked containers 12 to a central despatch location within the medical treatment facility where the containers 12 are off-loaded onto a transporter for transport to a medical waste disposal centre.

At the medical waste disposal centre, the containers 12 are unlocked, emptied and sterilized for return to the medical treatment facility for distribution therein by the cart 100.

A transporter for transporting the recyclable containers 12 from and to the central despatch location of a medical treatment facility is also such that the containers minimally contact each other during their transport so as to avoid the cost of buffing or polishing them to maintain their cosmetic appearance.

Figure 9:
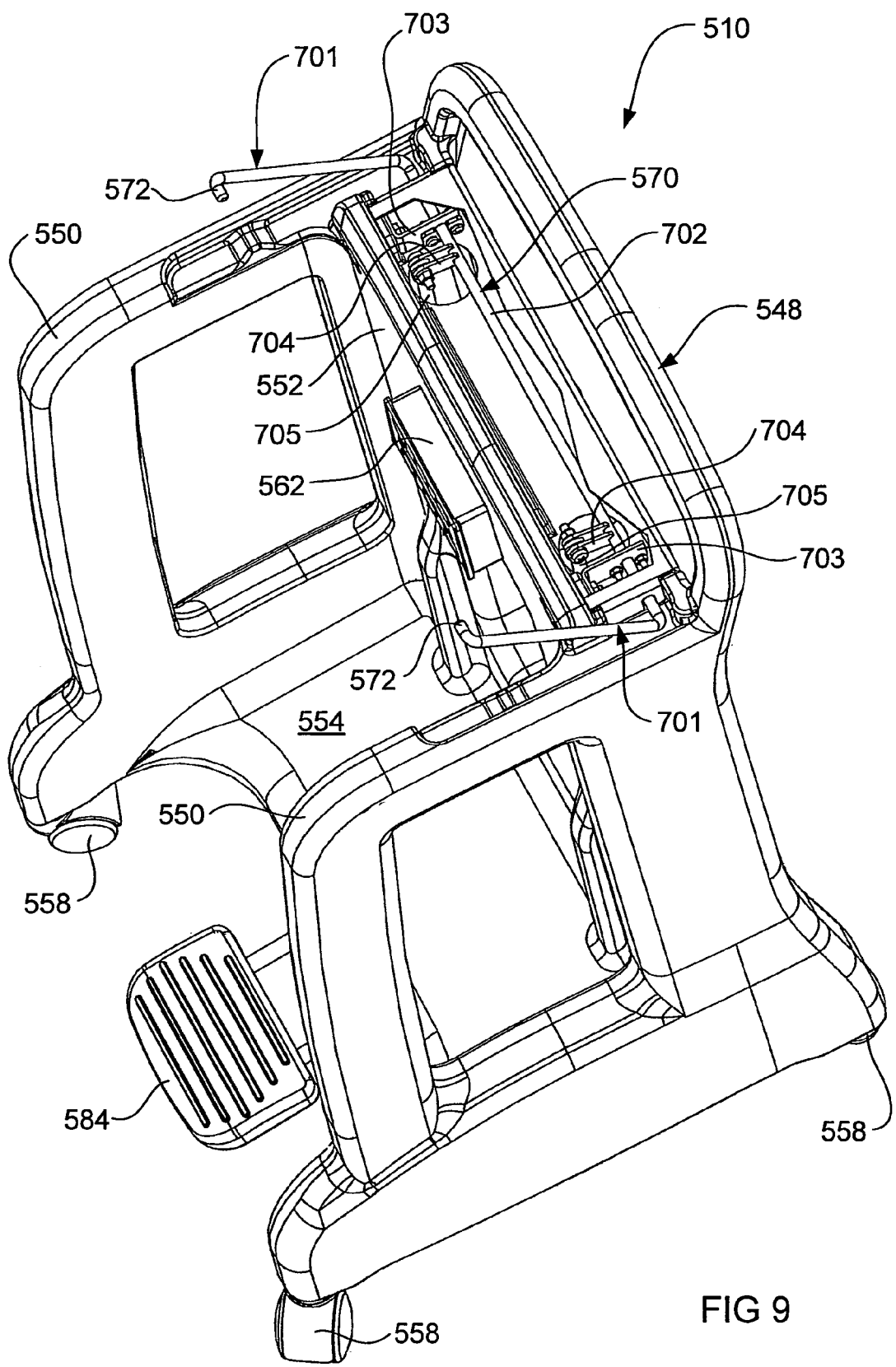
FIG. 9 is an isometric view of another embodiment of the trolley.
Figure 10:
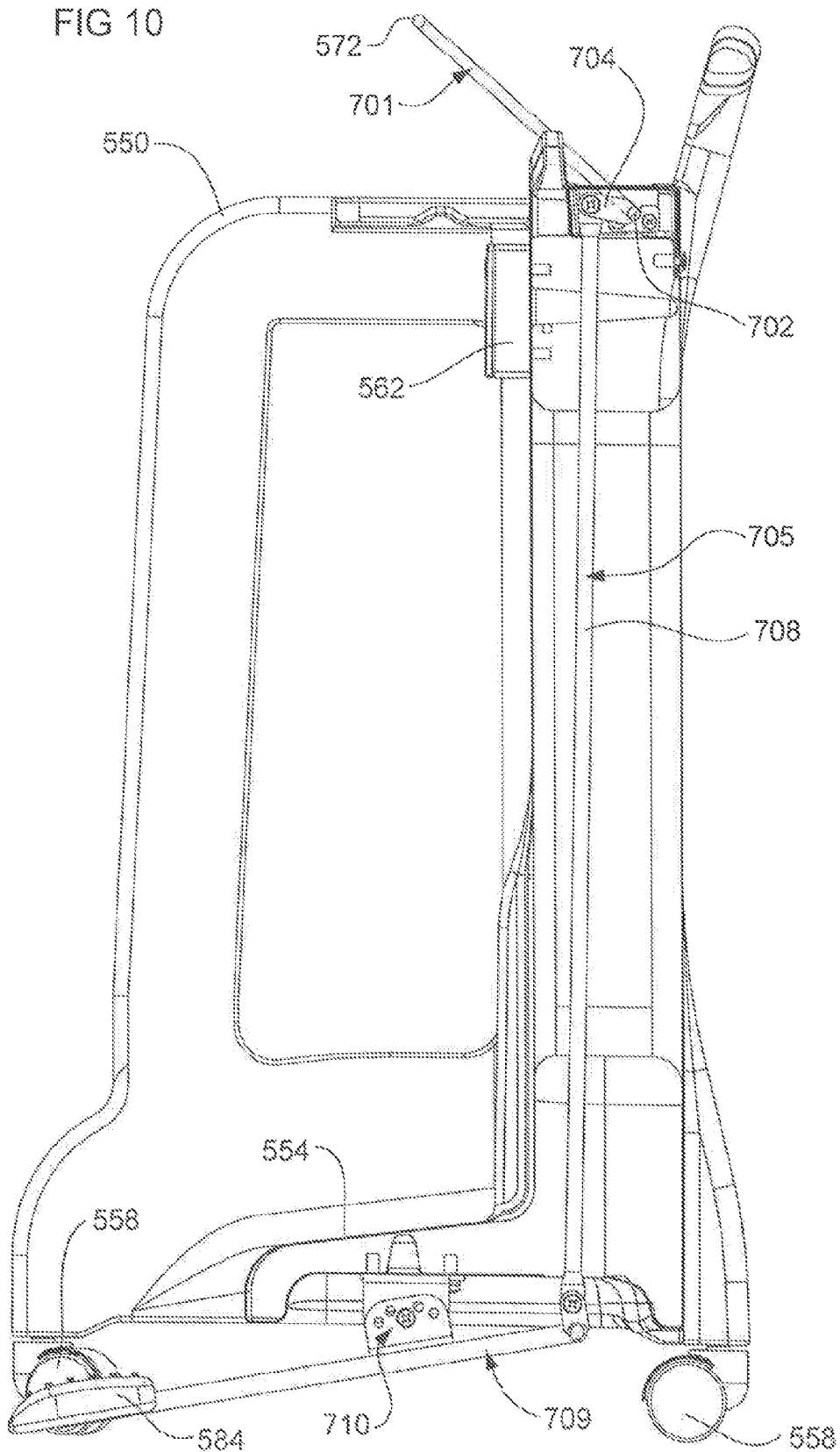
FIG. 10 is a cross sectional view through the trolley illustrated in FIG. 9.
Figure 11:
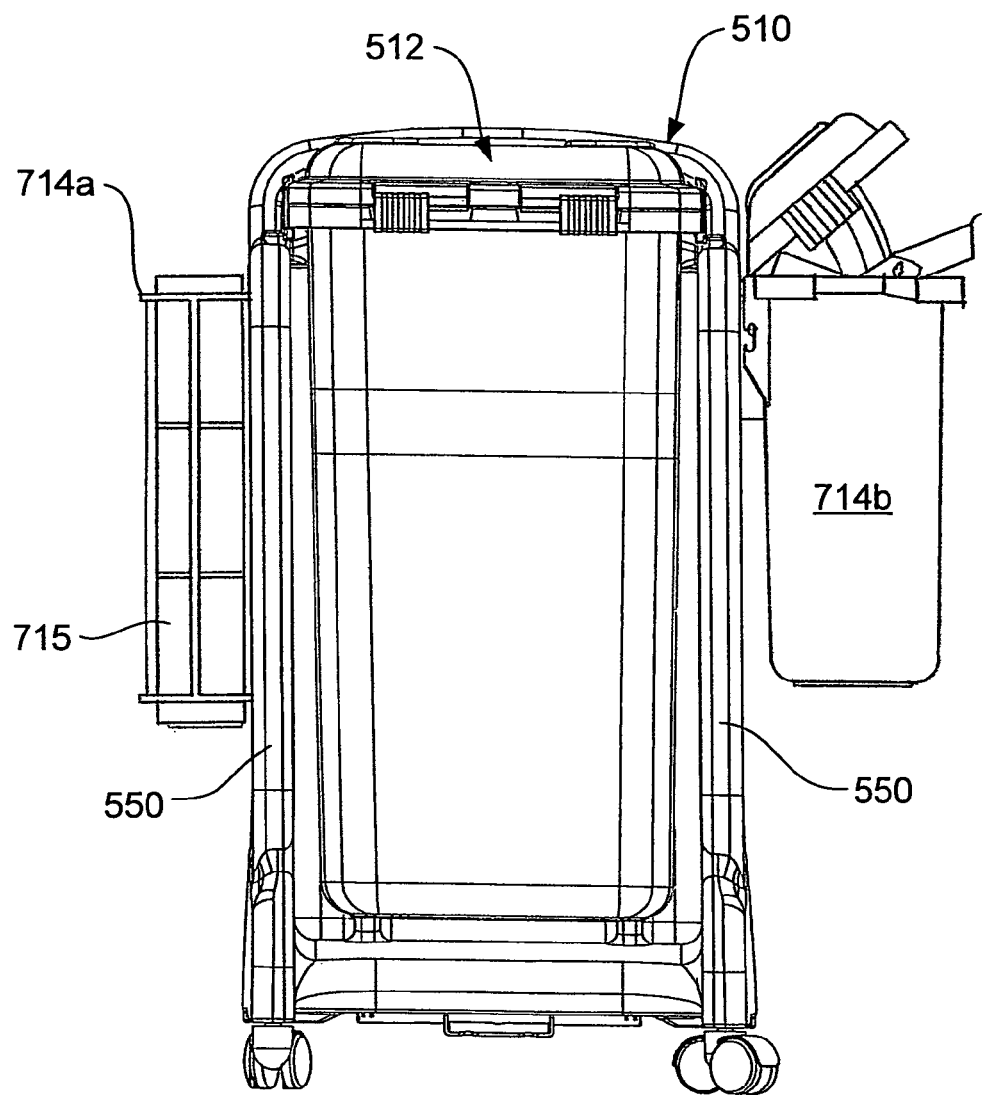
FIG. 11 is a front elevation view of the trolley from FIG. 9 with the container from FIG. 2 retained thereon and preferred components attached to the sides thereof.

Referring no to FIGS. 9, 10 and 11 which illustrate an alternate embodiment of a trolley according to the invention, where like features from the embodiment illustrated in FIGS. 1 to 6 are given like reference numerals with the prefix of "5". FIG. 9 illustrates a trolley 510, including a frame 548, sides 550, a rear wall 552 and a base 554, with four castor wheels 558 attached to the base.

A retainer 562 is fixed at the top of the frame 548 which is again sized and shaped to fit within the recess 36 in the rear surface 34 of the container 12 (see FIG. 3), when mounting the container 12 on the trolley 510. Whilst the retainer 562 illustrated in FIG. 8 does not show an upstanding tongue 96 (see FIG. 1), this embodiment could include this feature. Alternatively the retainer as illustrated in FIG. 9 has been positioned on the rear wall 552 so that the rear wall 552 provides the function of the tongue 96 in preventing over pivoting of the lid 16.

FIG. 9 again illustrates the member 570 in the form of a lever however the lever 570 illustrated includes a pair of arms 701, that are positionable in use on opposing sides of the container 12. Each arm 701 includes a lid engaging portion 572 at a free end thereof for engaging the undersurface portion 32 of the lid 16. The arms 701 are joined by a bar 702 that extends in a perpendicular direction to the arms 701 so that the bar 702 rotates about an axis that is perpendicular to the plane in which the arms 701 move. A pair of supports 703 attach the bar 702 to the rear wall 552 in such a way as to allow the bar 702 to rotate. The lever 570, in addition to the arms 701 and bar 702, also includes a pair of cranks 704 which make connection with linkages 705. The linkages 705 are in turn connected to the pedal 584 in a manner that will be described with reference to FIG. 10.

The linkage 705 may take any form and in the embodiment illustrated in FIG. 10 it includes substantially vertical rods 708 (only one is visible in cross section in FIG. 10) that move in a vertical direction to raise and lower the lever arms 701. A further lever arrangement 709 connects the rods 708 to the pedal 584 that pivots about a fulcrum connection 710. It ought to be appreciated that the location of the fulcrum 710 along the further lever 709 or the length of the crank may vary from that illustrated to allow for adjustment in the movement of the lid 16. Furthermore whilst the illustrations show screw connections between the further lever 709 and the rods 708, and the rods 708 with the cranks 704, these may be replaced by other forms of connections.

FIG. 10 illustrates the pedal 584 having been depressed to pivot the further lever 710 about the fulcrum 709. This causes the rods 708 to move upwards and to rotate the cranks 504. The cranks 504 rotate the bar 702 about the supports 702 to raise the arms 701, which in use opens the lid 16. The weight of the lid 16 preferably biases it towards a closed position despite the inertia of the arrangement from the arms 701 to the pedal 584 as previously described. A spring biasing means similar to the one used in the embodiment illustrated in FIG. 5 with the reference numeral 94 may be included to assist in this regard.

Referring now to FIG. 11 which illustrates the trolley 510 and a container 512 retained on the trolley 510. The figure also illustrates further components 714 mounted to outer surfaces of each of the sides 550 of the trolley 510. The components may take any form and in the preferred embodiment illustrated a receptacle 714a is mounted on the left hand side and a bin 714b is mounted to the right hand side. The receptacle 714a may retain boxes 715 of medical products, such as boxes of medial gloves, and it may be securely fastened to the trolley 510 by any suitable means. The bin 714b may be in the form of a sharps bin for receiving used sharp medical devices such as needles. The bin 714b may be securely fastened to the trolley 510 as per the receptacle 714a, or it may be retained using the retainer 562 as previously described with reference to the container 512. If the bin 714b is retained this will allow for it to be detached from the trolley 510.

It is to be understood that various alterations, additions and/or modifications may be made to the parts previously described without departing from the ambit of the present invention, and that, in the light of the above teachings, the present invention may be implemented in a variety of manners as would be understood by the skilled person.

The present application may be used as a basis for priority in respect of one or more future applications, and the claims of any such future application may be directed to any one feature or combination of features that are described in the present application. Any such future application may include one or more of the following claims, which are given by way of example and are non-limiting with regard to what may be claimed in any future application.

The invention claimed is:

1. A trolley for a container for medical waste, the container having a receptacle for receiving medical waste and a lid for sealing the receptacle, the lid being pivotable between an open position and a closed position, the lid and receptacle being shaped so that an undersurface portion of the lid is accessible when the lid is in the closed position, wherein the receptacle has a top lip that has a cut away section and the undersurface portion of the lid is part of a component on the lid that projects over the cut away section, the trolley including:
- a retainer for retaining the container on the trolley, and
- a member having a lid engaging portion, the member being operable so that the lid engaging portion engages the undersurface portion of the component on the lid and pivots the lid from the closed position to the open position,
- wherein the retainer and member are relatively located such that when the container is installed on the trolley and retained by the retainer, the lid engaging portion becomes positioned adjacent the undersurface portion of the component on the lid without requiring manual manipulation of the member or lid, and the projection of the component over the cut away section of the receptacle allows the undersurface portion to remain accessible when the lid is in the closed position.

2. The trolley as claimed in claim 1, wherein the member is operable by a foot pedal.

3. The trolley as claimed in 2, wherein the pedal is biased so that the member allows the lid to return to the closed position.

4. The trolley as claimed in claim 2 including a cable extending between the foot pedal and the member.

5. The trolley member according to claim 2 including a linkage between the foot pedal and the member.

6. The trolley as claimed in claim 1 wherein the member is a lever.

7. The trolley as claimed in claim 6 wherein the lever pivots in a plane and the lid engaging portion extends transverse to the plane.

8. The trolley as claimed in claim 6, wherein the lid engaging portion is positioned to engage the undersurface portion of the lid which is located on a side of the container.

9. The trolley as claimed in claim 6 wherein the lever includes a pair of arms that are locatable on opposing sides of the container when engaging the undersurface portion of the lid.

10. The trolley as claimed in claim 9 wherein each arm moves in a separate plane where each plane is substantially parallel with each other, and the arms pivot about an axis that is substantially perpendicular to each plane.

11. The trolley as claimed in claim 1, wherein the retainer is shaped to allow the container to be installed downwards on the trolley.

12. The trolley as claimed in claim 1, wherein the retainer is a bracket.

13. The trolley as claimed in claim 12, wherein the bracket has an extension to prevent over-pivoting of the lid.

14. The trolley according to claim 1, wherein the lid includes a lock having a slidable member that slides over the lid relative to a locked position whereby the lid is retained in the closed position when the slidable member is in the locked position, the slidable member includes a surface that forms the undersurface portion of the lid.

15. The trolley according to claim 1, including a further retainer for retaining a component to an outer surface of the trolley.

16. The trolley according to claim 1, including a receptacle for receiving medical products attached to an outer surface of the trolley.

17. An apparatus for medical waste including:
- a container having a receptacle for receiving medical waste and a lid for sealing the receptacle, the lid being pivotable between an open position and a closed position, the lid and receptacle being shaped so that an undersurface portion of the lid is accessible when the lid is in the closed position, wherein the receptacle has a top lip that has a cut away section and the undersurface portion of the lid is part of a component on the lid that projects over the cut away section, wherein the projection of the component over the cut away section of the receptacle allows the undersurface portion to remain accessible when the lid is in the closed position, and
- wherein the container is installed on a trolley for medical waste, the trolley includes a retainer for retaining the container on the trolley and a member having a lid engaging portion,
- wherein the member is operable so that the lid engaging portion engages the undersurface portion of the component on the lid and pivots the lid from the closed position to the open position, and
- wherein the retainer and member are relatively located such that when the container is installed on the trolley and retained by the retainer, the lid engaging portion becomes positioned adjacent the undersurface portion of the component on the lid without requiring manual manipulation of the member or lid.

18. The apparatus according to claim 17 wherein the lid includes a lock having a slidable member that slides over the lid relative to a locked position whereby the lid is retained in the closed position when the slidable member is in the locked position, the slidable member includes a surface that forms the undersurface portion of the lid.

19. The apparatus as claimed in claim 17, wherein the lid of the container is biased closed.

\* \* \* \* \*